United States Patent [19]

Murphy

[11] Patent Number: 4,925,665
[45] Date of Patent: May 15, 1990

[54] GLUCOSE FREE PRIMARY ANTICOAGULANT FOR BLOOD CONTAINING CITRATE IONS

[75] Inventor: Scott Murphy, Ardmore, Pa.

[73] Assignee: Thomas Jefferson University, Philadelphia, Pa.

[21] Appl. No.: 369,842

[22] Filed: Jun. 22, 1989

[51] Int. Cl.$^5$ .............................................. A61K 35/14
[52] U.S. Cl. ...................................... 424/532; 435/2; 424/529
[58] Field of Search ............................ 424/101; 435/2

[56] References Cited

U.S. PATENT DOCUMENTS

| | | | |
|---|---|---|---|
| 4,447,415 | 5/1984 | Rock | 424/101 |
| 4,695,460 | 9/1987 | Holme | 424/101 |
| 4,828,976 | 5/1989 | Murphy | 435/2 |

OTHER PUBLICATIONS

Huestis et al., Chem. Abst., vol. 87 (1977), p. 115,480v.
Soloway et al., Chem. Abst., vol. 79 (1973), p. 16312v.
Oldurova, Chem. Abst., vol. 67 (1967), p. 19282y.
Oldurova, Chem. Abst., vol. 56 (1962), p. 9266g.
Vinograd-Finkel et al., Chem. Abst., vol. 60 (1964), p. 4564g.
Murphy et al., "Improved Storage of Platelets for Transfusion in a New Container", Blood 60(1):94–200, Jul. 1982.
Murphy, "The Preparation and Storage of Platelets for Transfusion", Mammon, Barnhart, Lusher & Walsh Publication Ltd., Westbury, NY (1980).
Murphy, "Platelet Transfusion", Progress in Hemostasis and Thrombosis, vol. III, Edited by Theodore Spaet, Grune & Stratton, Inc. (1976).
Murphy et al., "Platelet Storage at 22° C.; Role of Gas Transport Across Plastic Containers in Maintenance of Viability", Blood 46(2):209–218 (1975).
Kilkson, Holme & Murphy, "Platelet Metabolism During Storage of Platelet Concentrates at 22° C.", Blood 64(2):406–414 (1984).
Murphy, "Platelet Storage for Transfusion", Seminars in Hematology 22(3):165–177 (1985).
Simon et al., "Extension of Platelet Concentrate Storage", Transfusion 23:207–212 (1983).
Cesar et al., "Plasma Free Fatty Acid Metabolism During Storage of Platelet Concentrates for Transfusion", Transfusion 27(5):434–437 (1987).
Mollison, "P.L. Blood Transfusion in Clinical Medicine", 7th Edition Blackwell, 1983.

Primary Examiner—Sam Rosen
Attorney, Agent, or Firm—Woodcock Washburn Kurtz Mackiewicz & Norris

[57] ABSTRACT

The present invention provides a novel primary citrate anticoagulant which is essentially free of glucose and its use to optimize the viability of stored platelets. The present invention allows platelets to be stored in plasma or synthetic media without the addition of buffer. Specifically the anticoagulant consists essentially of sodium citrate and citric acid.

9 Claims, 1 Drawing Sheet

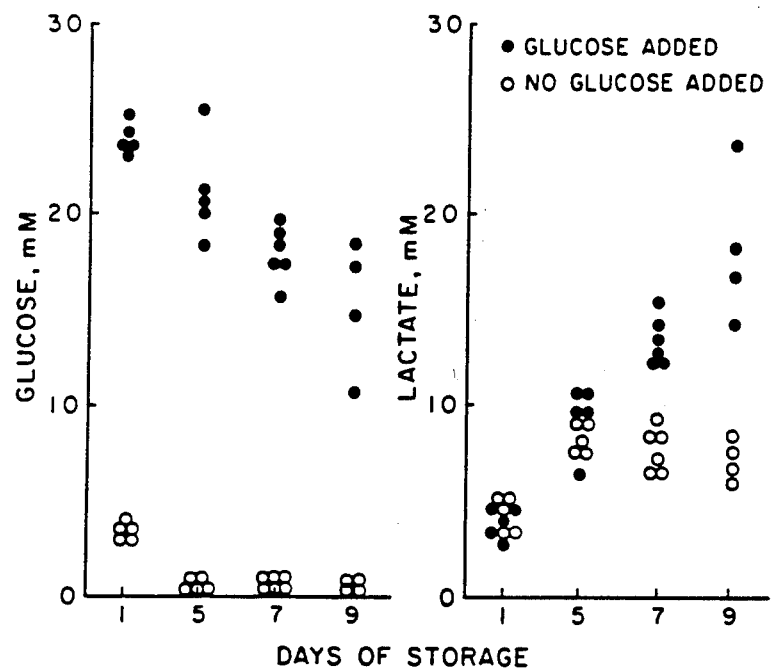

GLUCOSE FREE PRIMARY ANTICOAGULANT FOR BLOOD CONTAINING CITRATE IONS

This invention was made with Government support under a grant, HL 20818, awarded by the National Institutes of Health. The Government has certain rights in this invention.

This invention was disclosed in Disclosure Document No. 172533, filed June 25, 1987.

This application is related to application Ser. No. 284,987 filed Dec. 15, 1988 entitled "Glucose Free Media for Storing Blood Platelets" (Murphy) which is a division of application Ser. No. 905,277 filed Sept. 9, 1986 which is a continuation-in-part application Ser. No. 730,805 filed May 6, 1985, which in turn is a continuation-in-part of my copending applications Ser. Nos. 611,895, filed May 18, 1984 and 667,270, filed Nov. 1, 1984, which are respectively a division and a continuation of Ser. No. 566,709 filed Dec. 29, 1983, which in turn is a continuation-in-part of Ser. No. 550,251 filed Nov. 9, 1983, each of which applications is assigned to Thomas Jefferson University, assignee of the present application.

BACKGROUND OF THE INVENTION

The present invention relates to a novel primary anticoagulant for blood and its use in the preparation of platelets stored prior to transfusion into a patient. Platelets are obtained as a by product from whole blood donations and from plateletphersis procedures. Typically they are now stored at 22±2° C. in their own plasma within a plastic container whose walls are permeable to atmospheric gases. The plasma associated with these platelets normally contains all the ingredients of normal plasma plus ingredients in the primary anticoagulant which result in a dextrose concentration five times the physiologic concentration. The dextrose is added to the primary anticoagulant for the benefit of red cells which require it during storage, and dextrose is generally accepted to be required for platelet storage as well.

In routine blood banking practice, the primary anticoagulant which is utilized in citrate-phosphate-dextrose (CPD). CPD is composed of:

| | |
|---|---|
| trisodium citrate(dihydrate) | 26.30 g |
| citric acid (monohydrate) | 3.27 g |
| sodium dihydrogen phosphate (monohydrate) | 2.22 g |
| dextrose | 25.50 g |
| water to | 1 liter |

From Mollison, P. L., Blood Transfusion in Clinical Medicine, 7th Edition, Blackwell, 1983.

It is to be noted that the final concentration of the components of the anticoagulant in the platelet concentrate derived from the blood-anticoagulant mixture may be expressed as a millimolar (mM) concentration or as milliequivalents (meq) per liter. By convention, the final concentration of "citrate" has often been expressed as mM by adding the millimolar concentration of trisodium citrate and citric acid. Since citrate is an anion when in solution, the concentration when derived from several sources may more properly be expressed as meq per liter. For solutions of trisodium citrate and citric acid, the relationship between the two modes of expressing concentration is 3 equivalents per mole. Such an anticoagulant mixture of trisodium citrate and citric acid is referred to herein as acid citrate.

Donations of a unit of blood (63 ml of CPD mixed with 450 ml of whole blood) are processed by centrifugation into three fractions: red cells, plasma, and platelets. The volume of packed red cells from a unit of blood is approximately 180 ml with a remaining volume of plasma and anticoagulant of about 333 ml. As used in the remainder of this application, the term plasma includes any anticoagulant which has been added thereto at the time of blood collection. The red cells are typically suspended in approximately 45 ml of plasma. Platelets are suspended in approximately 50 ml of plasma. This platelet containing product is typically referred to as a platelet concentrate. The remaining 238 ml of plasma is frozen as fresh plasma.

A great deal is known about human platelt cells. General papers describing techniques, materials and methods for storage of platelets are described by Murphy et al. in "Improved Storage of Platelets for Transfusion in a New Container", Blood 60(1): 194–200 (July, 1982); by Murphy in "The Preparation and Storage of Platelets for Transfusion", Mammon, Barnhart, Lusher and Walsh, PJD Publications, Ltd., Westbury, N.Y. (1980); by Murphy in "Platelet Transfusion", Progress in Hemostasis and Thrombosis, Vol. III, Edited by Theodore Spaet, Grune and Stratton, Inc. (1976); by Murphy et al. in "Platelet Storage at 22° C.: Role of Gas Transport Across Plastic Containers in Maintenance of Viability", Blood 46(2): 209-218 (1975); by Kilkson, Holme and Murphy in "Platelet Metabolism During Storage of Platelet Concentrates at 22° C.", Blood 64(2): 406–414 (1984); by Murphy in "Platelet Storage for Transfusion", Seminars in Hematology 22(3): 165–177 (1985); by Simon, Nelson, Carmen and Murphy in "Extension of Platelet Concentrate Storage", Transfusion 23: 207–212 (1983); by Cesar, Diminno, Alam, Silver and Murphy in "Plasma Free Fatty Acid Metabolism During Storage of Platelet Concentrates for Transfusion", Transfusion 27(5): 434–437 (1987); each of which publications is hereby incorporated by reference as if more fully set forth herein.

There exists a considerable body of prior art concerning storage of platelets. Prior work has shown that the duration of platelet storage is limited by the continuing production of lactic acid from dextrose by the platelets. Although this provides energy for the platelets, the lactic acid acidifies the medium, which acidity eventually destroys the platelets. It has also been shown that platelets consume oxygen during storage for energy production, the end product of which process is a gas, $CO_2$ which, unlike lactic acid, can leave the platelet concentrate through the plastic walls of the container in which it is normally stored. The production of $CO_2$ does not acidify the storage medium for the platelets. In addition to the glycolysis of dextrose, fatty acids and amino acids typically present in the plasma may be used as substrates for oxidative metabolism of stored platelet cells.

However, most platelet storage media contain glucose. In U.S. Pat. No. 4,695,460 (Holme), a synthetic platelet storage media is disclosed containing 3.0–7.5 grams of dextrose, 3.0–6.0 grams of sodium citrate, and 2.0–4.2 grams of sodium bicarbonate. U.S. Pat. No. 4,447,415 (Rock) discloses a number of storage solutions, all but one containing glucose. The one non-glucose containing solution contains trypsin which would be deleterious to the survival of platelets. It has been appreciated that platelet storage in a medium essentially free of glucose could be advantageous. For example, in U.S. Pat. No. 4,828,976, Murphy discloses a glucose free media for storing blood platelets. To store platelets for periods in excess of 5 days, it is taught that the storage media should be essentially free of glucose. It is also disclosed that it is the presence of glucose that leads to the generation of lactic acid which adversely affects platelet viability. However, Murphy utilized the conventional glucose-containing primary anticoagulant and omitted glucose only from the storage media.

The anticoagulants currently used for blood donations are designed to optimize the subsequent storage of red blood cells. The acidity of the citrate-citric acid mixture yields pH, approximately 7.1, in the anticoagulated blood. Higher pHs speed red blood cell glycolysis and lower pHs speed 2,3 DPG disappearance. The final citrate concentration, however, is 40% higher than that actually required to anticoagulate the blood. Glucose is added so that its final concentration in the anticoagulated blood is 25 mM thus providing substrate for red cell glycolysis.

Many of these conditions which have been conventionally employed may not be optimal for the preparation and storage of platelet concentrates (PC) Since red cell additive solutions are coming into widespread use, new primary anticoagulants should be designed to optimize platelet transfusion therapy.

Notwithstanding the considerable work conducted in this area, a need still exists for means to improve the storage of platelets in a viable condition.

SUMMARY OF THE INVENTION

The present invention provides a novel primary citrate anticoagulant which does not contain dextrose and its use to improve the viability of stored platelets. There are advantages for omitting glucose from the primary anticoagulant. When platelets are stored in glucose, the glucose is converted to lactic acid leading to a deleterious fall in pH. However, only a small fraction of metabolic energy is derived from this glycolysis, most being derived from oxidation of non-glucose substrates. Thus, it is advantageous for the residual plasma to contain only the glucose present in the circulation of the donor and not added glucose in the primary anticoagulant. Therefore, in the present invention, acid citrate is present as primary anticoagulant. With dextrose omitted, platelet storage may be improved in both plasma and synthetic storage media. In plasma, a limiting factor for long term storage is that lactic acid production exceeds the bicarbonate buffering capacity leading to lethal pH fall at day 10–14 of storage. This will not occur if the primary anticoagulant is not supplemented with glucose. With dextrose omitted, there is also no need to add buffer to the platelet storage medium, as is required when the primary anticoagulant contains dextrose. The present invention allows platelets to be stored in a medium which need not contain buffer or a glycolytic inhibitor to control pH fall due to lactic acid production. Therefore, this invention would be useful to store platelets in plasma long term or in a synthetic medium without the need to add a buffer. New additive solutions such as Adsol or Nutricel make it unnecessary to have glucose present in the primary anticoagulant for the benefit of red blood cells. Once the red cells have been separated, an appropriate additive can be added to optimize storage of these cells as well.

Accordingly, the present invention provides a primary anticoagulant which optimizes platelet preparation and storage. As a result, the subject primary anticoagulant is designed to optimize platelet transfusion therapy.

A further object of the present invention is the use of a novel primary anticoagulant to optimize platelet storage.

This and further objects of the present invention will become apparent from the following more detailed description.

DESCRIPTION OF THE DRAWINGS

FIG. 1 is a graph of glucose and lactate concentrations (in mM) versus the days of storage for paired PC in plasma prepared with and without glucose in the primary anticoagulant.

DETAILED DESCRIPTION OF THE INVENTION

In order to maintain viability, platelets must generate new adenosine triphosphate (ATP) continuously to meet their energy needs. Two pathways are normally available: glycolysis and oxidative phosphorylation. In glycolysis, one molecule of glucose is converted to two molecules of lactic acid to generate two molecules of ATP. In oxidation, glucose, fatty acid or amino acid enters the citric acid cycle and is converted to $CO_2$ and water. This pathway requires the presence of an adequate supply of oxygen. It is much more efficient than glycolysis. Oxidative metabolism of glucose to $CO_2$ and water yields 36 molecules of ATP.

It has been recognized that platelets will meet their energy needs in a manner which is not necessarily consistent with their long term storage in a viable condition. When given adequate oxygen, platelets produce most of their ATP through oxidation, but continue to produce lactic acid instead of diverting all metabolized glucose through the oxidative pathway. During the storage of platelets in plasma, lactic acid concentrations rise at approximately 2.5 mM per day. See Murphy et al.; "Platelet Storage at 22° C., Blood 46(2): 209–218 (1975); Murphy, "Platelet Storage for Transfusion", Seminars in Hematology 22(3): 165–177 (1985). This leads to gradual fall in pH. As explained in the aforementioned Murphy articles, when lactic acid reaches about 20 mM, the pH which started at 7.2 may reach 6.0. Since platelet viability is irreversibly lost if pH falls to 6.1 or below, a major limiting variable for platelet storage is pH. At this rate of lactic acid production, pH would fall much more rapidly if it were not for naturally occurring plasma buffers, principally sodium bicarbonate.

In the present invention glucose is omitted from the primary anticoagulant to optimize platelet viability during storage. For example between 12 and 50 meq. of citrate ion is added per a unit of blood and more specifically 21.3 meq. The precent of citric acid relative to total citrate is 10 to 50% and more specially 14.8%. To examine the effect of omission of glucose on platelets during storage, an acid citrate anticoagulant was prepared by removing 8.75 ml anticoagulant from a phlebotomy container in which 50 ml 4% $Na_3$ Citrate was the primary anticoagulant (Fenwal Lab, Deerfield, Ill.) and adding 33.75 ml of 85 mM citric acid. This provided the same sodium citrate and citric acid concentration as is present in acid-citrate-dextrose (ACD) anticoagulant. See Mollison, P. L. Blood Transfusion in Clinical Medicine, 7th Edition, Blackwell, 1983. A donor then underwent double plateletpheresis to obtain paired PC. For each paired study, one of each pair of such PC received supplemental glucose (final concentration, 25 mM). As shown in FIG. 1, residual glucose in donor plasma in the unsupplemented PC was consumed between day 1 and day 5. After day 5, lactate concentration decreased to a slight but statistically significant extent, $0.35 +/- 0.13$ (SD) mM per day $p<0.01$. Using a paired t test, the only major difference between PC with and without glucose was a rise in pH from days 5 through 9 without glucose due to the absence of lactate production. The platelets which were prepared without supplemental glucose were well maintained as assessed by standard techniques such as platelet count, platelet volume, dispersion, extent of shape change, platelet aggregation, and microscopic morphology. The present invention therefore provides a primary anticoagulant which optimizes platelet viability.

What is claimed is:

1. A primary anticoagulant preparation for addition to a human blood platelet preparation consisting essentially of sodium citrate and citric acid and being essentially free of glucose wherein the total amount of citrate anion in said anticoagulant for a blood donation of a unit of blood is between 12 and 50 meq.

2. The anticoagulant of claim 1 wherein the total amount of citrate anion in the anticoagulant is 21.3 meq.

3. The anticoagulant of claim 1 wherein the percentage of citric acid relative to total citrate is 10 to 50%.

4. The anticoagulant of claim 3 wherein the percentage of citric acid relative to total citrate is 14.8%.

5. A method of human blood platelet preparation to improve platelet storage consisting essentially of:
adding a primary anticoagulant consisting essentially of sodium citrate and citric acid wherein the total amount of citrate anion in said anticoagulant for a blood donation of a unit of blood is between 12 and 50 meq and being essentially free of glucose.

6. The method of claim 5 wherein the step of adding anticoagulant is performed so as to ensure that the amount of citrate anion in the anticoagulant is 21.3 meq.

7. The method of claim 5 wherein the step of adding the anticoagulant is performed so as to ensure that the percentage of citric acid relative to total citrate is 10 to 50%.

8. The method of claim 7 wherein the step of adding the anticoagulant is performed so as to ensure that the percentage of citric acid relative to total citrate is 14.8%.

9. The method of claim 5 wherein the step of adding the anticoagulant is performed to bring the pH of the final platelet concentrate to a pH greater than 6.1.

* * * * *